(12) United States Patent
Beyer et al.

(10) Patent No.: US 7,838,749 B2
(45) Date of Patent: Nov. 23, 2010

(54) METHOD FOR IMPROVING THE AGRONOMIC AND NUTRITIONAL VALUE OF PLANTS

(75) Inventors: Peter Beyer, Heitersheim (DE); Ingo Potrykus, Magden (CH)

(73) Assignee: Syngenta Participations AG, Basel (CH)

( * ) Notice: Subject to any disclaimer, the term of this patent is extended or adjusted under 35 U.S.C. 154(b) by 202 days.

(21) Appl. No.: 12/144,224

(22) Filed: Jun. 23, 2008

(65) Prior Publication Data

US 2008/0276332 A1      Nov. 6, 2008

Related U.S. Application Data

(63) Continuation of application No. 09/914,913, filed as application No. PCT/EP00/01850 on Mar. 3, 2000, now abandoned.

(30) Foreign Application Priority Data

Mar. 5, 1999    (DE) ................. 199 09 637

(51) Int. Cl.
*A01H 5/00*    (2006.01)
*A01H 5/10*    (2006.01)
*C12N 15/29*   (2006.01)
*C12N 15/31*   (2006.01)
*C12N 15/52*   (2006.01)
*C12N 15/82*   (2006.01)

(52) U.S. Cl. .................. 800/320.2; 800/282; 800/287; 800/288; 435/419; 435/468

(58) Field of Classification Search ........... None
See application file for complete search history.

(56) References Cited

FOREIGN PATENT DOCUMENTS

WO      WO 99/07867      * 2/1999

OTHER PUBLICATIONS

Burkhardt P. et al., in Rice Genetics III; Proceeding of the Third International Rice Genetics Symposium; International Rice Research Institute (IRRI), 1996; Khush G. S. ed.*
P. Burkhardt et al., in Rice Genetics III, Proceeding of the Third International Rice Symposium, International Rice Research Institute (IRRI), 1996; Khush G.S. ed, pp. 818-820.
The Rockfeller Foundation, International Program on Rice Biotechnology, Workshop Report Jun. 10-11, 1993. Potential for Carotenoid Biosynthesis in Rice Endosperm.
X. Ye et al., Science, Jan. 14, 2000; vol. 287, pp. 303-305.
P. Lodato et al., Applied and Environmental Microbiology, Aug. 2003, vol. 69, No. 8; pp. 4676-4682.
A. Velayos et al., Eur. J. Biochem., 2000, vol. 267, pp. 5509-5519.
P.M. Bramley, Pure and Appl. Chem., 1997, vol. 69, No. 10; pp. 2159-2162.
G.E. Bartley et al., Eur. J. Biochem., Jan. 1999, vol. 259, pp. 396-403.
G. Bartley et al., The Journal of Biological Chemistry, Dec. 5, 1993, vol. 268, No. 34, pp. 25718-25721.
P. Fraser et al., Plant Molecular Biology, 1999, vol. 40, pp. 687-698.
I. Potrykus, Plant Physiology, Mar. 2001, vol. 125, pp. 1157-1161.

* cited by examiner

*Primary Examiner*—Russell Kallis
(74) *Attorney, Agent, or Firm*—S. Matthew Edwards

(57) ABSTRACT

The present invention provides means and methods of transforming plant cells, seeds, tissues or whole plants in order to yield transformants capable of expressing all enzymes of the carotenoid biosynthesis pathway that are essential for the targeted host plant to accumulate carotenes and/or xanthophylls of interest. The present invention also provides DNA molecules designed to be suitable for carrying out the method of the invention, and plasmids or vector systems comprising said molecules. Furthermore, the present invention provides transgenic plant cells, seeds, tissues and whole plants that display an improved nutritional quality and contain such DNA molecules and/or that have been generated by use of the methods of the present invention.

11 Claims, 5 Drawing Sheets

METHOD FOR IMPROVING THE AGRONOMIC AND NUTRITIONAL VALUE OF PLANTS

This is a continuation application of U.S. application Ser. No. 09/914,913, filed Dec. 17, 2001 now abandoned, a national stage application under 35 U.S.C. §371 of International Application No. PCT/EP0001850, filed on Mar. 3, 2000, which is entitled to the benefit of German Application No. 19909637.6, filed on Mar. 5, 1999, which are incorporated by reference in their entireties.

The present invention relates to the field of transformation of plant cells, seeds, tissues and whole plants. More specifically, the present invention relates to the insertion of recombinant nucleotide sequences encoding one or more of the enzymes specific of the carotenoid biosynthetic pathway into plant material in order to improve its agronomic and nutritional value.

BACKGROUND OF THE INVENTION

Provitamin A (β-carotene) deficiency represents a very serious health problem leading to severe clinical symptoms in the part of the worlds population living on grains such as rice as the major or almost only staple food. In south-east Asia alone, it is estimated that 5 million children develop the eye disease xerophthalmia every year, of which 0.25 million eventually go blind (Sommer, 1988; Grant, 1991). Furthermore, although vitamin A deficiency is not a proximal determinant of death, it is correlated with an increased susceptibility to potential fatal afflictions such as diarrhoea, respiratory diseases and childhood diseases, such as measles (Grant, 1991). According to statistics compiled by UNICEF, improved provitamin nutrition could prevent 1-2 million deaths annually among children aged 1-4 years, and an additional 0.25-0.5 million deaths during later childhood (Humphrey et al., 1992). For these reasons it is very desirable to raise the carotenoid levels in staple foods. Moreover, carotenoids are known to assist in the prevention of several sorts of cancer and the role of lutein and zeaxanthin in the retina preventing macula degeneration is established (see e.g. Brown et al., 1998; Schalch, 1992).

Furthermore, carotenoids have a wide range of applications as colorants in human food and animal feed as well as in pharmaceuticals. In addition there is increasing interest in carotenoids as nutriceutical compounds in "functional food". This is because some carotenoids, e.g. β-carotene, exhibit provitamin-A character in mammals.

Carotenoids are 40-carbon ($C_{40}$) isoprenoids formed by condensation of eight isoprene units derived from the biosynthetic precursor isopentenyl diphosphate (see FIG. 1). By nomenclature, carotenoids fall into two classes, namely carotenes, comprising hydrocarbons whereas oxygenated derivatives are referred to as xanthophylls. Their essential function in plants is to protect against photo-oxidative damage in the photosynthetic apparatus of plastids. In addition they participate in light harvesting during photosynthesis and represent integral components of photosynthetic reaction centers. Carotenoids are the direct precursors of the phytohormone abscisic acid.

Carotenoid biosynthesis as schematically depicted in FIG. 1 has been investigated and the pathway has been elucidated in bacteria, fungi and plants (see for example, Britton, 1988). In plants, carotenoids are formed in plastids.

The early intermediate of the carotenoid biosynthetic pathway is geranylgeranyl diphosphate (GGPP), formed by the enzyme geranylgeranyl diphosphate synthase from isopentenyl diphosphate (IPP) and dimethylallyl diphosphate (DMAPP, see FIG. 1). The subsequent enzymatic step, also representing the first carotenoid-specific reaction, is catalyzed by the enzyme phytoene synthase. The reaction comprises a two-step reaction resulting in a head-to head condensation of two molecules of GGPP to form the first, yet uncoloured carotene product, phytoene (Dogbo et al., 1988, Chamovitz et al., 1991; Linden et al., 1991; Pecker et al., 1992). Phytoene synthase occurs in two forms soluble/inactive and membrane-bound/active and it requires vicinal hydroxyfunctions for activity as present in the surface of plastid galactolipid-containing membranes (Schledz et al., 1996).

While the formation of phytoene is similar in bacteria and plants, the metabolization of phytoene differs pronouncedly. In plants, two gene products operate in a sequential manner to generate the coloured carotene lycopene (Beyer et al., 1989). They are represented by the enzymes phytoene desaturase (PDS, see e.g. Hugueney et al., 1992) and ζ-carotene desaturase (ZDS, see e.g. Albrecht et al., 1996). Each introduces two double bonds yielding ζ-carotene via phytofluene and lycopene via neurosporene, respectively. PDS is believed to be mechanistically linked to a membrane-bound redox chain (Nievelstein et al., 1995) employing plastoquinone (Mayer et al., 1990; Schulz et al., 1993; Norris et al., 1995), while ZDS acts mechanistically in a different way (Albrecht et al., 1996). In plants, the entire pathway seems to involve cis-configured intermediates (Bartley et al., 1999). In contrast, in many bacteria, such as in the genus *Erwinia*, the entire desaturation sequence forming all four double bonds is achieved by a single gene product (CrtI), converting phytoene to lycopene directly (see e.g. Miawa et al., 1990; Armstrong et al., 1990, Hundle et al., 1994). This type of bacterial desaturase is known not to be susceptible to certain bleaching herbicides which efficiently inhibit plant-type phytoene desaturase.

In plants, two gene products catalyze the cyclization of lycopene, namely α(ε)- and β-lycopene cyclases, forming α(ε)- and β-ionone end-groups, respectively (see e.g. Cunningham et al., 1993; Scolnik and Bartley, 1995, Cunningham et al., 1996). In plants, normally β-carotene carrying two β-ionone end-groups and α-carotene, carrying one α(ε) and one β-ionone end-group are formed.

The formation of the plant xanthophylls is mediated first by two gene products, α- and β-hydroxylases (Masamoto et al., 1998) acting in the position C3 and C3' of the carotene backbone of α- and β-carotene, respectively. The resulting xanthophylls are named lutein and zeaxanthin.

Further oxygenation reactions are catalyzed by zeaxanthin epoxydase catalyzing the introduction of epoxy-functions in position C5,C6 and C5',C6' of the zeaxanthin backbone (Marin et al., 1996). This leads to the formation of antheraxanthin and violaxanthin. The reaction is made reversible by the action of a different gene product, violaxanthin de-epoxydase (Bugos and Yamamoto, 1996).

The gene product leading to the formation of neoxanthin remains to be identified.

Genes and cDNAs coding for carotenoid biosynthesis genes have been cloned from a variety of organisms, ranging from bacteria to plants. Bacterial and cyanobacterial genes include *Erwinia herbicola* (Application WO91/13078, Armstrong et al., 1990), *Erwinia uredovora* (Misawa et al., 1990), *R. capsulatus* (Armstrong et al., 1989), *Thermus thermophilus* (Hoshino et al., 1993), the cyanobacterium *Synechococcus sp.* (Genbank accession number X63873), *Flavobacterium sp.* strain R1534 (Pasamontes et al., 1997). Genes and cDNAs coding for enzymes in the carotenoid biosynthetic pathway in higher plants have been cloned from various sources, including *Arabidopsis thaliana, Sinalpis alba, Capsicuin annuum, Naricisstis pseudonarcissus, Lycopersicon esculentum*, etc., as can be deduced from the public databases.

Currently relatively little is known about the use of the cloned genes in higher plant transformations and the resulting effects. The expression of phytoene synthase from tomato can affect carotenoid levels in fruit (Bird et al., 1991; Brarley et al., 1992; Fray and Grier-son, 1993).

It has also been reported that constitutive expression of a phytoene synthase in transformed tomato plants results in dwarfism, due to redirecting the metabolite GGPP from the gibberellin biosynthetic pathway (Fray et al., 1995). No such problems were noted upon constitutively expressing phytoene synthase from *Narcissus pseudonarcissus* in rice endosperm (Burkhardt et al., 1997). *Erwinia uredovora* CrtI, as a bacterial desaturase, is known to function in plants and to confer bleaching-herbicide resistance (Misawa et al., 1993).

Many attempts have been made over the years to alter or enhance carotenoid biosynthetic pathways in various plant tissues such as vegetative tissues or seeds, or in bacteria. See, for example, WO 96/13149, WO 98/06862, WO 98/24300, WO 96/28014, and U.S. Pat. No. 5,618,988. All of these are restricted to the manipulation of pre-existing carotenoid biosynthetic reactions in the cells. Other applications aiming at altering carotenoid biosynthesis in oil-rich seeds are different, since they provide a sink to accommodate an excess of carotenoids formed due to the increase provoked by the transformation.

It is apparent that there is needed a method of transforming plant material in order to yield transformants capable of expressing all enzymes of the carotenoid biosynthesis pathway necessary to produce carotenes and xanthophylls of interest.

SUMMARY OF THE INVENTION

The present invention provides means and methods of transforming plant cells, seeds, tissues or whole plants in order to yield transformants capable of expressing all enzymes of the carotenoid biosynthesis pathway that are essential for the targeted host plant to accumulate carotenes and/or xanthophylls of interest. The present invention also provides DNA molecules designed to be suitable for carrying out the method of the invention, and plasmids or vector systems comprising said molecules. Furthermore, the present invention provides transgenic plant cells, seeds, tissues and whole plants that display an improved nutritional quality and contain such DNA molecules and/or that have been generated by use of the methods of the present invention.

Thus, the present invention provides both the de novo introduction and expression of carotenoid biosynthesis, which is particularly important with regard to plant material that is known to be essentially carotenoid-free, such as rice endosperm and the seeds of many other cereals, and the modification of pre-existing carotenoid biosynthesis in order to up- or down-regulate accumulation of certain intermediates or products of interest.

ABBREVIATIONS USED THROUGHOUT THE SPECIFICATION

Figure 1:
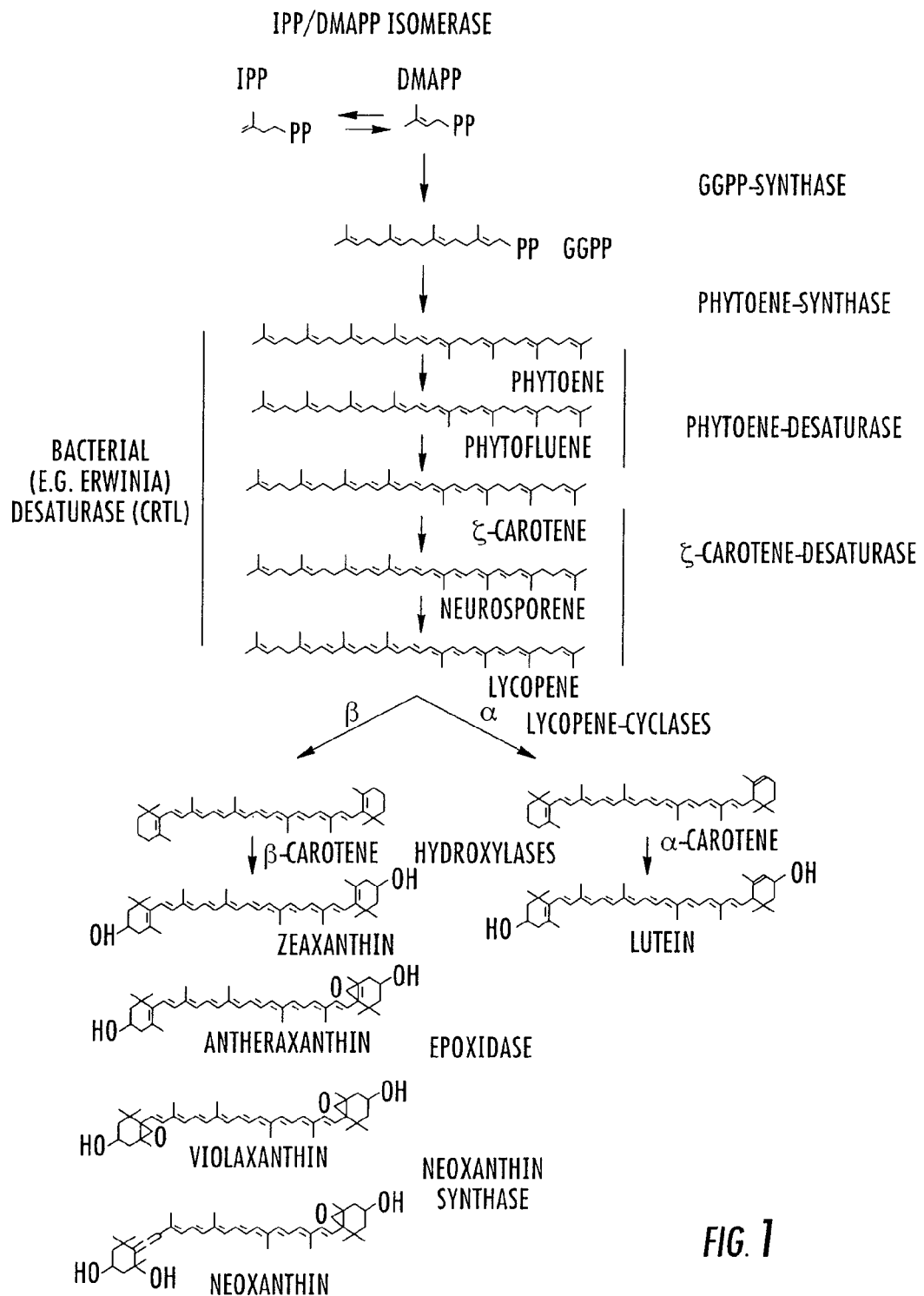
FIG. 1 shows a general pathway of plant carotenoid biosynthesis. Enzyme names are given in bold. Also indicated is the reaction catalyzed by a bacterial CrtI-type carotene desaturase.

The systematic names of relevant carotenoids mentioned herein are:
Phytoene: 7,8,11,12,7',8',11',12'-octahydro-ψ,ψ-carotene
Phytofluene: 7,8,11,12,7',8',-hexahydro-ψ, ψ-carotene
ζ-carotene: 7,8,7',8'-tetrahydro-ψ,ψ-carotene
Neurosporene: 7,8,-dihydro-ψ,ψ-carotene
Lycopene: ψ, ψ-carotene
β-carotene: β,β-carotene
α-carotene: β,ε-carotene
Zeaxanthin: β,β-carotene-3,3'-diol
Lutein: β,ε-carotene-3,3'-diol
Antheraxanthin: 5,6-epoxy-5,6-dihydro-β,β-carotene-3,3'-diol
Violaxanthin: 5,6,5',6'-diepoxy-5,6,5',6',tetrahydro-β,β-carotene-3,3'-diol
Neoxanthin: 5',6'-epoxy-6,7-didehdro-5,6,5',6'-tetrahydro-β,β-carotene-3,5,3'-triol Enzymes:
PSY: phytoene synthase
PDS: phytoene desaturase
CrtI: bacterial carotene desaturase
ZDS: ζ (zeta)-carotene desaturase
CYC: lycopene β-cyclase Non-Carotene Intermediates:
IPP: isopentenyl diphosphate
DMAPP: dimethylallyl-diphosphate
GGPP: geranylgeranyl diphosphate As used herein, the term "plant" generally includes eukaryotic alga, embryophytes including *Bryophyta, Pteridoplyta* and Spermatophyta such as *Gymnospermae* and *Angiospermae*, the latter including *Magnoliopsida, Rosopsida* (eu-"dicots"), *Liliopsida* ("monocots"). Representative and preferred examples include grain seeds, e.g. rice, wheat, barley, oats, amaranth, flax, triticale, rye, corn, and other grasses; oil seeds, such as oilseed *Brassica* seeds, cotton seeds, soybean, safflower, sunflower, coconut, palm, and the like; other edible seeds or seeds with edible parts including pumpkin, squash, sesame, poppy, grape, mung beans, peanut, peas, beans, radish, alfalfa, cocoa, coffee, hemp, tree nuts such as walnuts, almonds, pecans, chick-peas etc. Furthermore, potatoes carrots, sweet potatoes, tomato, pepper, cassava, willows, oaks, elm, maples, apples, bananas; ornamental flowers such as lilies, orchids, sedges, roses, buttercups, petunias, phlox, violets, sunflowers, and the like. Generally, the present invention is applicable in ornamental species as well as species cultivated for food, fibre, wood products, tanning materials, dyes, pigments, gums, resins, latex products, fats, oils, drugs, beverages, and the like. Preferably, the target plant selected for transformation is cultivated for food, such as, for example, grains, roots, legumes, nuts, vegetables, tubers, fruits, spices and the like.

DETAILED DESCRIPTION OF THE INVENTION

In accordance with the subject invention, means and methods of transforming plant cells, seeds, tissues or whole plants are provided to produce transformants capable of expressing all enzymes of the carotenoid biosynthesis pathway that are essential for the targeted host plant to accumulate carotenes and/or xanthophylls of interest. According to another aspect of the present invention, said methods can also be used to modify pre-existing carotenoid biosynthesis in order to up- or down-regulate accumulation of certain intermediates or products of interest. Furthermore, specific DNA molecules are provided which comprise nucleotide sequences carrying one or more expression cassettes capable of directing production of one or more enzymes characteristic for the carotenoid biosynthesis pathway selected from the group consisting of:

phytoene synthase derived from plants, fungi or bacteria,
phytoene desaturase derived from plants, fungi or bacteria,
ζ-carotene desaturase derived from plants or cyanobacteria, and
lycopene cyclase derived from plants, fungi or bacteria.

According to a preferred embodiment, the above expression cassette comprises one or more genes or cDNAs coding for plant, fungi or bacterial phytoene synthase, plant, fungi or bacterial phytoene desaturase, plant ζ-carotene desaturase, or plant, fungi or bacterial lycopene cyclase, each operably linked to a suitable constitutive, inducible or tissue-specific promoter allowing its expression in plant cells, seeds, tissues or whole plants. Particularly preferred genes or cDNAs code for plant phytoene synthase, bacterial phytoene desaturase or plant lycopene cyclase. A large, still increasing number of genes coding for phytoene synthase (plant and bacterial), CrtI-type carotene desaturase (bacterial) and lycopene cyclase (plant and bacterial) have been isolated and are accessible from the databases. They are from various sources and they are all available for use in the methods of the present invention.

It is preferred that the DNA molecules further comprise at least one selectable marker gene or cDNA operably linked to a suitable constitutive, inducible or tissue-specific promoter, with hygromycin phosphotransferase as the selectable marker under the control of a constitutive promoter being most preferred. Although the skilled person may select any available promoter functionally active in plant material, it is preferred in the design of appropriate expression cassettes according to the invention to operably link the respective nucleotide sequence encoding phytoene desaturase, ζ-carotene desaturase, or lycopene cyclase to tissue-specific or constitutive promoters, whereas the nucleotide sequence encoding phytoene synthase is preferably expressed under the control of a tissue-specific promoter to avoid interference with gibberellin-formation.

It is to be understood that the nucleotide sequence as a functional element of the DNA molecule according to the invention can comprise any combination of one or more of the above-mentioned genes or cDNAs. In a particularly preferred embodiment of the present invention, said nucleotide sequence comprises functional expression cassettes for both phytoene synthase and bacterial or fungi phytoene desaturase, and can after incorporation into an appropriate plasmid or vector system (plasmid A) be introduced into target plant material, either alone or together with a second vector (plasmid B) comprising a nucleotide sequence which codes for lycopene cyclase.

The invention further provides plasmids or vector systems comprising one or more of the above DNA molecules or nucleotide sequences, which preferably are derived from *Agrobacterium tumefaciens*.

The subject invention additionally provides transgenic plant cells, seeds, tissues and whole plants that display an improved nutritional quality and contain one or more of the above DNA molecules, plasmids or vectors, and/or that have been generated by use of the methods according to the present invention.

Figure 2:
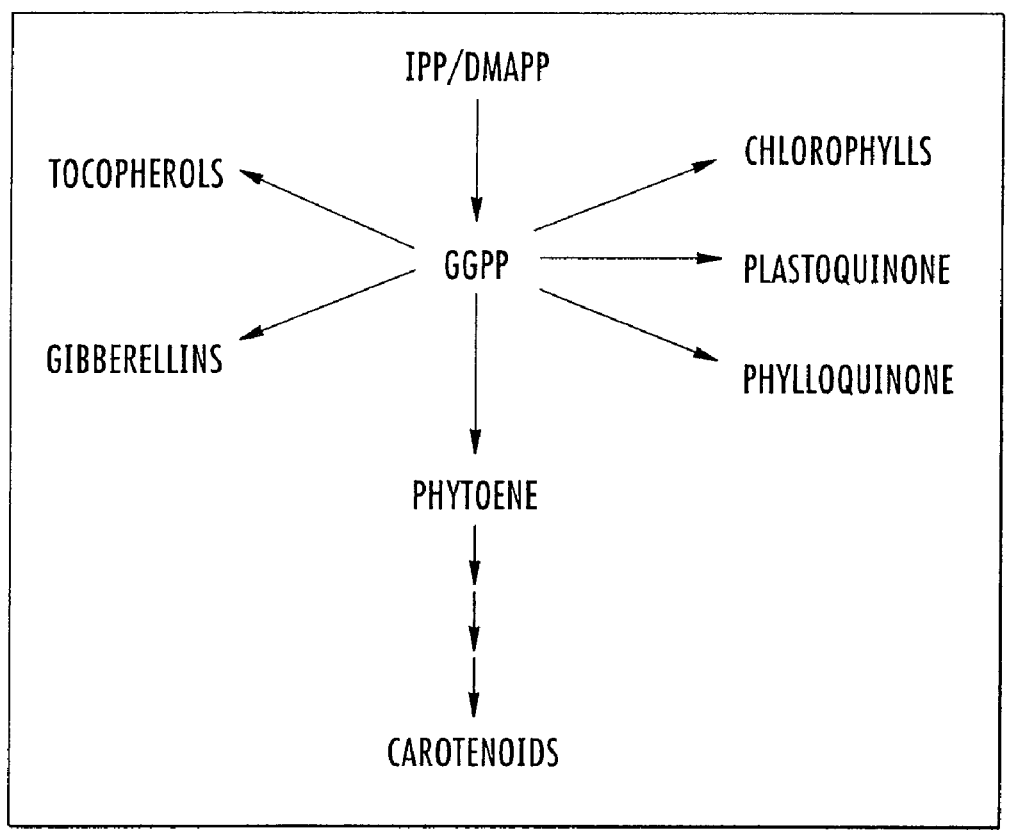
FIG. 2 indicates that the intermediate geranylgeranyl diphosphate (GGPP) is not only involved in carotenoid biosynthesis, but serves as a building block in pathways leading to different compounds via prenylation reactions (e.g. tocopherols, quinones, chlorophylls) or by different reaction not employing non-pRenyl acceptor molecules (e.g. gibberellins, flavor and aroma substances).

The current invention is based on the fact that the early intermediate geranylgeranyl diphosphate (GGPP) does not only serve for carotenogenesis but represents a branching point serving several different biosynthetic pathways (FIG. 2). It is therefore concluded that this precursor occurs in the plastids of all plant tissues, carotenoid-bearing or not, such as rice endosperm. The source of GGPP can thus be used to achieve the objects of the present invention, i.e. the introduction of the carotenoid biosynthetic pathway in part or as a whole, and/or the enhancement or acceleration of a pre-existing carotenoid biosynthetic pathway.

The term "carotenoid-free" used throughout the specification to differentiate between certain target plant cells or tissues shall mean that the respective plant material not transformed according to the invention is known normally to be essentially free of carotenoids, as is the case for e.g. storage organs such as, for example, rice endosperm and the like. Carotenoid-free does not mean that those cells or tissues that accumulate carotenoids in almost undetectable amounts are excluded. Preferably, said term shall define plant material having a carotenoid content of 0.001% w/w or lower.

With regard to the selection of appropriate sources from which carotenoid pathway enzymes can be derived, it is to be understood that coding sequences from *Cyanobacteria* being homologous to respective plant sequences can also be used in accordance with the present invention.

In a preferred embodiment of the present invention a higher plant phytoene synthase is operatively linked to a promoter conferring tissue-specific expression. This is unified on the same plasmid (plasmid A) with a bacterial (Crt-I-type) phytoene desaturase, the latter fused to a DNA sequence coding for a transit peptide and operatively linked to a promoter allowing constitutive expression. The transformation of plants with this construct in a suitable vector will direct the formation of lycopene in the tissue selected by the promoter controlling phytoene synthase, for example, in the seeds of carotenoid-free cereal seeds. Surprisingly, this transformation alone can initiate carotenoid synthesis beyond lycopene formation towards downstream xanthophylls, such as lutein, zeaxanthin, antheraxanthin, violaxanthin, and neoxanthin, even in a carotenoid-free tissue such as rice endosperm. In addition the formation of α-carotene is observed. Thus, a carotenoid complement similar to the one present in green leaves is formed. This unexpected phenomenon (here also termed "overshoot"-mechanism) may be due to the constitutive expression of the respective later genes (lycopene cyclases, β-carotene hydroxylases, epoxidases). which become activated by the transformation-mediated substrate supply or, alternatively by the induction of the expression of carotenoid biosynthetic genes provoked by the transformation. In the case that the "overshoot" mechanism does not function, the co-transformation (plasmid B) with a gene or cDNA coding for lycopene cyclase can overcome this problem and enable at least α- or β-carotene (provitamin A)-formation. In cases where the "overshoot" mechanism functions, this co-transformation can increase the effects provoked by phytoene synthase and the CrtI-type carotene desaturase. The present invention thus includes the introduction of the carotenoid biosynthetic pathway beyond the point given genetically by transforming with plasmid A or A plus B.

Plasmid A is also capable in enhancing carotenoid production in carotenoid-bearing tissues. These transformations lead to enhancing the nutritional value of human food and animal feed. A further advantage of using bacterial phytoene desaturase of the crtI-type in the transformation is that said enzyme will be expressed also in leaf chloroplasts, thereby conferring resistance to bleaching herbicides targeting plant phytoene desaturase. The present invention thus also includes to exploit bleaching herbicide resistance in conjunction with transgenic plants carrying at least plasmid A.

The second plasmid B may carry the gene for a plant lycopene cyclase; alternatively a bacterial lycopene cyclase, equipped with a transit-sequence may be used. This is operatively linked to a promoter, preferably conferring the same tissue-specificity of expression as with phytoene synthase in plasmid A. The co-transformation of plasmid A and B results in the complementing the target tissue such as root. fruit tuber or seed with the full information for carrying out the carotenoid biosynthetic pathway from geranylgeranyl diphosphate to form β-carotene. In the case of pre-existing or induced later reactions of the pathway this co-transformation (see above) enables enhanced carotenoid content and enhanced formation of β-carotene-derived xanthophylls.

All genes used are operatively equipped with a DNA sequence coding for a transit-sequence allowing plastid-import. This is done either by recombinant DNA technology or the transit-sequence is present in the plant cDNA in use. The transformation then allows carotenoid formation using a pool of the precursor geranylgeranyl-diphosphate localized in plastids. This central compound is neither a carotenoid nor does it represent a precursor that is solely devoted to carotenoid biosynthesis (see FIG. 2).

The plants should express the gene(s) introduced, and are preferably homozygous for expression thereof. Generally, the gene will be operably linked to a promoter functionally active in the targeted host cells of the particular plant. The expression should be at a level such that the characteristic desired from the gene is obtained. For example, the expression of the selectable marker gene should provide for, an appropriate selection of transformants yielded according to the methods of the present invention. Similarly, the expression of one or more genes of the carotenoid and xanthophyll biosynthetic pathway for enhanced nutritional quality should result in a plant having a relatively higher content of one or more of the pathway intermediates or products compared to that of the same species which is not subjected to the transformation method according to the present invention. On the other hand, it will generally be desired to limit the excessive expression of the gene or genes of interest in order to avoid significantly adversely affecting the normal physiology of the plant, i.e. to the extent that cultivation thereof becomes difficult.

The gene or genes encoding the enzyme or enzymes of interest can be used in expression cassettes for expression in the transformed plant tissues. To achieve the objects of the present invention, i.e., to introduce or complement the carotenoid biosynthetic pathway in a target plant of interest, the plant is transformed with at least one expression cassette comprising a transcriptional initiation region linked to a gene of interest.

The transcriptional initiation may be native or analogous to the host or foreign or heterologous to the host. By foreign is intended that the transcriptional initiation region is not found in the wild-type host into which the transcriptional initiation region is introduced.

Of particular interest are those transcriptional initiation regions associated with storage proteins, such as glutelin, patatin, napin, cruciferin, β-conglycinin, phaseolin, or the like.

The transcriptional cassette will include, in 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from other sources. Convenient termination regions are available from the Ti-plasmid of *A. tumefaciens* such as the octopine synthase and nopaline synthase termination regions (see also, Guerineau et al., 1991; Proudfoot, 1991; Sanfacon et al., 1991, Mogen et al., 1990; Munroe et al., 1990; Ballas et al., 1989; Joshi et al., 1987).

For the most part, the gene or genes of interest of the present invention will be targeted to plastids, such as chloroplasts, for expression. In this manner, where the gene of interest is not directly inserted into the plastid, the expression cassette will additionally contain a sequence encoding a transit peptide to direct the gene of interest to the plastid. Such transit peptides are known in the art (see, for example, Von Heijne et al., 1991; Clark et al., 1989; Della-Cioppa et al., 1987; Romer et al., 1993; and, Shah et al., 1986. Any carotenoid pathway genes useful in the invention can utilize native or heterologous transit peptides.

The construct can also include any other necessary regulators such as plant translational consensus sequences (Joshi, 1987), introns (Luehrsen and Walbot, 1991) and the like, operably linked to the nucleotide sequence of interest. Intron sequences within the gene desired to be introduced may increase its expression level by stabilizing the transcript and allowing ist effective translocation out of the nucleus. Among the known such intron sequences are the introns of the plant ubiquitin gene (Cornejo, 1993). Furthermore, it has been observed that the same construct inserted at different loci on the genome can vary in the level of expression in plants. The effect is believed to be due at least in part to the position of the gene on the chromosome, i.e., individual isolates will have different expression levels (see, for example, Hoever et al., 1994). Further regulatory DNA sequences thai may be used for the construction of expression cassettes include, for example, sequences that are capable of regulating the transcription of an associated DNA sequence in plant tissues in the sense of induction or repression.

There are, for example, certain plant genes that are known to be induced by various internal and external factors, such as plant hormones, heat shock, chemicals, pathogens, oxygen deficiency, light, stress, etc.

A further group of DNA sequences which can be regulated comprises chemically-driven sequences that are present, for example, in the PR (pathogenesis-related) protein genes of tobacco and are inducible by means of chemical regulators such as those described in EP-A 0 332 104.

Yet another consideration in expression of foreign genes in plants is the level of stability of the transgenic genome, i.e., the tendency of a foreign gene to segregate from the population. If a selectable marker is linked to the gene or expression cassette of interest, then selection can be applied to maintain the transgenic plant.

It may be beneficial to include 5' leader sequences in the expression cassette construct. Such leader sequences can act to enhance translation. Translation leaders are known in the art and include: picornavirus leaders, for example, EMCV leader (Encephalomyocarditis 5' noncoding region; Elroy-Stein et al., 1989); potyvirus leaders, for example, TEV leader (Tobacco Etch Virus; Allisson et al., 1986); and human immunoglobulin heavy-chain binding protein (BiP, Macejak and Sarnow, 1991); untranslated leader from the coat protein mRNA of alfalfa mosaic virus (AMV RNA 4; Jobling and Gehrke 1987); tobacco mosaic virus leader (TMV; Gallie et al., 1989); and maize chlorotic mottle virus leader (MCMV; Lommel et al., 1991; see also, Della-Cioppa et al., 1987).

Depending upon where the DNA sequence of interest is to be expressed, it may be desirable to synthesize the sequence with plant preferred codons, or alternatively with chloroplast preferred codons. The plant preferred codons may be determined from the codons of highest frequency in the proteins expressed in the largest amount in the particular plant species of interest (see, EP-A 0 359 472; EP-A 0 386 962; WO 91/16432; Perlak et al., 1991; and Murray et al., 1989). In this manner, the nucleotide sequences can be optimized for expression in any plant. It is recognized that all or any part of the gene sequence may be optimized or synthetic. That is, synthetic or partially optimized sequences may also be used. For the construction of chloroplast preferred genes, see U.S. Pat. No. 5,545,817.

In preparing the transcription cassette, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

The expression cassette carrying the gene of interest is placed into an expression vector by standard methods. The selection of an appropriate expression vector will depend upon the method of introducing the expression vector into host cells. A typical expression vector contains: prokaryotic DNA elements coding for a bacterial replication origin and an antibiotic resistance gene to provide for the growth and selection of the expression vector in the bacterial host; a cloning site for insertion of an exogenous DNA sequence, which in this context would code for one or more specific enzymes of the carotenoid biosynthetic pathway; eukaryotic DNA elements that control initiation of transcription of the exogenous gene, such as a promoter; and DNA elements that control the processing of transcripts, such as a transcription termination/poly-adenylation sequence. It also can contain such sequences as are needed for the eventual integration of the vector into the chromosome.

In a preferred embodiment, the expression vector also contains a gene encoding a selection marker such as, e.g. hygromycin phosphotransferase (van den Elzen et al., 1985), which is functionally linked to a promoter. Additional examples of genes that confer antibiotic resistance and are thus suitable as selectable markers include those coding for neomycin phosphotransferase kanamycin resistance (Velten et al., 1984); the kananycin resistance (NPT II) gene derived from Tn5 (Bevan et al., 1983); the PAT gene described in Thompson et al., (1987); and chloramphenicol acetyltransferase. For a general description of plant expression vectors and selectable marker genes suitable according to the present invention, see Gruber et al., (1993). As outlined above, it is also possible to omitt a further selection marker from an expression cassette comprising bacterial crtI, the gene product of which has shown to confer resistance to bleaching herbicides. In this specific embodiment, it is preferred that crtI is under the control of a constitutive or tissue-specific promoter. In a highly preferred embodiment, crtI is controlled by a promoter specific for and functionally active in green photosynthetically active tissues or cells.

A promoter element employed to control expression of the gene of interest and the marker gene, respectively, can be any plant-compatible promoter. Those can be plant gene promoters, such as the promoter for the small subunit of ribulose-1, 5-bis-phosphate carboxylase (RUBISCO), or promoters from tumour-inducing plasmids of *Agrobacterium tumefaciens*, like that nopaline synthase and octopine synthase promoters, or viral promoters such as the cauliflower mosaic virus (CaMV) 19S and 35S promoters or the figwort mosaic virus 35S promoter. See international application WO 91/19806, for example, for a review of known plant promoters which are suitable for use in the present invention.

"Tissue-specific" promoters provide that accumulation of one or more of said gene products is particularly high in the tissue in which products of the carotenoid or xanthophyll biosynthetic pathway shall be expressed; some expression may occur in other parts of the plant. Examples of known tissue-specific promoters include the glutelin 1 promoter (Kim et al., 1993; Okita et al., 1989; Zheng et al., 1993), the tuber-directed class I patatin promoter (Bevan et al., 1986); the promoters associated with potato tuber ADPGPP genes (Muller et al., 1990); the soybean promoter of β-conglycinin, also known as the 7S protein, which drives seed-directed transcription (Bray, 1987); and seed-directed promoters from the zein genes of maize endosperm (Pedersen et al., 1982). A further type of promoter which can be used according to the invention is a plant ubiquitin promoter. Plant ubiquitin promoters are well known in the art, as evidenced by Kay et al., (1987), and EP-A 0 342 926. Equally suitable for the present invention are actin promoters, histone promoters and tubulin promoters. Examples of preferred chemically inducible promoters, such as the tobacco PR-1a promoter, are detailed in EP-A 0 332 104. Another preferred category of promoters is that which is wound inducible. Preferred promoters of this kind include those described by Stanford et al., (1989), Xu et al., (1993), Logemann et al., (1989), Rohrmeier & Lehle, (1993), Firek et al., (1993), and Warner et al., (1993).

The plant cells, seeds, tissues and whole plants contemplated in the context of the present invention may be obtained by any of several methods. Those skilled in the art will appreciate that the choice of method might depend on the type of plant, i.e. monocot or dicot, targeted for transformation. Such methods generally include direct gene transfer, chemically-induced gene transfer, electroporation, microinjection (Crossway et al., 1986; Neuhaus et al., 1987), *Agrobacterium*-mediated gene transfer, ballistic particle acceleration using, for example, devices available from Agracetus, Inc, Madison, Wis., and Dupont, Inc., Wilmington, Del. (see, for example, Sanford et al., U.S. Pat. No. 4,945,050; and Mc Cabe et al., 1988), and the like.

One method for obtaining the present transformed plants or parts thereof is direct gene transfer in which plant cells are cultured or otherwise grown under suitable conditions in the presence of DNA oligonucleotides comprising the nucleotide sequence desired to be introduced into the plant or part thereof The donor DNA source is typically a plasmid or other suitable vector containing the desired gene or genes. For convenience, reference is made herein to plasmids, with the understanding that other suitable vectors containing the desired gene or genes are also contemplated.

Any suitable plant tissue which takes up the plasmid may be treated by direct gene transfer. Such plant tissue includes, for example, reproductive structures at an early stage of development, particularly prior to meiosis, and especially 1-2 weeks pre-meiosis. Generally, the pre-meiotic reproductive organs are bathed in plasmid solution, such as, for example, by injecting plasmid solution directly into the plant at or near the reproductive organs. The plants are then self-pollinated, or cross-pollinated with pollen from another plant treated in the same manner. The plasmid solution typically contains about 10-50 μg DNA in about 0.1-10 ml per floral structure, but more or less than this may be used depending on the size of the particular floral structure. The solvent is typically sterile water, saline, or buffered saline, or a conventional plant medium. If desired, the plasmid solution may also contain agents to chemically induce or enhance plasmid uptake, such as, for example, PEG, $Ca^{2+}$ or the like.

Following exposure of the reproductive organs to the plasmid, the floral structure is grown to maturity and the seeds are harvested. Depending on the plasmid marker, selection of the transformed plants with the marker gene is made by germination or growth of the plants in a marker-sensitive, or preferably a marker-resistant medium. For example, seeds obtained from plants treated with plasmids having the kanamycin resistance gene will remain green, whereas those without this marker gene are albino. Presence of the desired gene transcription of mRNA therefrom and expression of the peptide can further be demonstrated by conventional Southern, northern, and western blotting techniques.

In another method suitable to carry out the present invention, plant protoplasts are treated to induce uptake of the plasmid. Protoplast preparation is well-known in the art and typically involves digestion of plant cells with cellulase and other enzymes for a sufficient period of time to remove the cell wall. Typically, the protoplasts are separated from the digestion mixture by sieving and washing. The protoplasts are then suspended in an appropriate medium, such as, for example, medium F, CC medium, etc., typically at $10^4$-$10^7$ cells/ml. To this suspension is then added the plasmid solution described above and an inducer such as polyethylene glycol, $Ca^{2+}$, Sendai virus or the like. Alternatively, the plasmids may be encapsulated in liposomes. The solution of plasmids and protoplasts are then incubated for a suitable period of time, typically about 1 hour at about 25° C. In some instances, it may be desirable to heat shock the mixture by briefly heating to about 45° C., e.g. for 2-5 minutes, and rapidly cooling to the incubation temperature. The treated protoplasts are then cloned and selected for expression of the desired gene or genes, e.g. by expression of the marker gene and conventional blotting techniques. Whole plants are then regenerated from the clones in a conventional manner.

The electroporation technique is similar except that electrical current is typically applied to the mixture of naked plasmids and protoplasts, in an electroporation chamber in the absence or presence of polyethylene glycol, $Ca^{2+}$ or the like. Typical electroporation includes 1-10 pulses of 40-10,000 DC volts for a duration of 1-2000 us with typically 0.2 second intervals between pulses. Alternating current pulses of similar severity can also be used. More typically, a charged capacitor is discharged across the electroporation chamber containing the plasmid protoplast suspension. This treatment results in a reversible increase in the permeability of biomembranes and thus allows the insertion of the DNA according to the invention. Electroporated plant protoplasts renew their cell wall, divide and form callus tissue (see, for example, Riggs et al., 1986).

Another method suitable for transforming target cells involves the use of *Agrobacterium*. In this method, *Agrobacterium* containing the plasmid with the desired gene or gene cassettes is used to infect plant cells and insert the plasmid into the genome of the target cells. The cells expressing the desired gene are then selected and cloned as described above. For example, one method for introduction of a gene of interest into a target tissue, e.g., a tuber, root, grain or legume, by means of a plasmid, e.g. an Ri plasmid and an *Agrobacterium*, e.g. *A. rhizogenes* or *A. tumefaciens*, is to utilize a small recombinant plasmid suitable for cloning in *Escierichia coli*, into which a fragment of T-DNA has been spliced. This recombinant plasmid is cleaved open at a site within the T-DNA. A piece of "passenger" DNA is spliced into this opening. The passenger DNA consists of the gene or genes of this invention which are to be incorporated into the plant DNA as well as a selectable marker, e.g., a gene for resistance to an antibiotic. This plasmid is then recloned into a larger plasmid and then introduced into an *Agrobacterium* strain carrying an unmodified Ri plasmid. During growth of the bacteria, a rare double-recombination will sometimes take place resulting in bacteria whose T-DNA harbours an insert: the passenger DNA. Such bacteria are identified and selected by their survival on media containing the antibiotic. These bacteria are used to insert their T-DNA (modified with passenger DNA) into a plant genome. This procedure utilizing *A. rhizogenes* or *A. tumefaciens* give rise to transformed plant cells that can be regenerated into healthy, viable plants (see, for example, Hinchee et al., 1988).

Another suitable approach is bombarding the cells with microprojectiles that are coated with the transforming DNA (Wang et al., 1988), or are accelerated through a DNA containing solution in the direction of the cells to be transformed by a pressure impact thereby being finely dispersed into a fog with the solution as a result of the pressure impact (EP-A 0 434 616).

Microprojectile bombardment has been advanced as an effective transformation technique for cells, including cells of plants. In Sanford et al., (1987), it was reported that microprojectile bombardment was effective to deliver nucleic acid into the cytoplasm of plant cells of Allium cepa (onion). Christou et al., (1988) reported the stable transformation of soybean callus with a kanamycin resistance gene via microprojectile bombardment. The same authors reported penetration at approximately 0.1% to 5% of cells and found observable levels of NPTII enzyme activity and resistance in the transformed calli of up to 400 mg/l of kanamycin. McCabe et al., (1988) report the stable transformation of Glycine max (soybean) using microprojectile bombardment. McCabe et al. further report the recovery of a transformed $R_1$ plant from an $R_o$ chimaeric plant (also see, Weissinger et al., 1988; Datta et al., 1990 (rice); Klein et al., 1988a (maize); Klein et al., 1988b (maize); Fromm et al., 1990; and Gordon-Kamm et al., 1990 (maize).

Alternatively, a plant plastid can be transformed directly. Stable transformation of chloroplasts has been reported in higher plants, see, for example, SVAB et al., (1990); SVAB and Maliga, (1993); Staub and Maliga, (1993). The method relies on particle gun delivery of DNA containing a selectable marker and targeting of the DNA to the plastid genome through homologous recombination. In such methods, plastid gene expression can be accomplished by use of a plastid gene promoter or by trans-activation of a silent plastid-borne transgene positioned for expression from a selective promoter sequence such as recognized by T7 RNA polymerase. The silent plastid gene is activated by expression of the specific RNA polymerase from a nuclear expression construct and targeting the polymerase to the plastid by use of a transit peptide. Tissue-specific expression may be obtained in such a method by use of a nuclear-encoded and plastid-directed specific RNA polymerase expressed from a suitable plant tissue-specific promoter. Such a system has been reported in McBride et al., (1994).

The list of possible transformation methods given above by way of example is not claimed to be complete and is not intended to limit the subject of the invention in any way.

The present invention therefore also comprises transgenic plant material, selected from the group consisting of protoplasts, cells, calli, tissues, organs, seeds, embryos, ovules, zygotes, etc. and especially, whole plants, that has been transformed by means of the method according to the invention and comprises the recombinant DNA of the invention in expressible form, and processes for the production of the said transgenic plant material.

Positive transformants are regenerated into plants following procedures well-known in the art (see, for example, McCormick et al., 1986). These plants may then be grown, and either pollinated with the same transformed strainer or different strains before the progeny can be evaluated for the presence of the desired properties and/or the extent to which the desired properties are expressed and the resulting hybrid having the desired phenotypic characteristic identified. A first evaluation may include, for example, the level of bacterial/fungal resistance of the transformed plants. Two or more generations may be grown to ensure that the subject phenotypic characteristic is stably maintained and inherited and then seeds harvested to ensure the desired phenotype or other property has been achieved.

Further comprised within the scope of the present invention are transgenic plants, in particular transgenic fertile plants transformed by means of the method of the invention and their asexual and/or sexual progeny, which still display the new and desirable property or properties due to the transformation of the mother plant.

The term 'progeny' is understood to embrace both, "asexually" and "sexually" generated progeny of transgenic plants. This definition is also meant to include all mutants and variants obtainable by means of known processes, such as for example cell fusion or mutant selection and which still exhibit the characteristic properties of the initial transformed plant, together with all crossing and fusion products of the transformed plant material.

Parts of plants, such as for example flowers, stems, fruits, leaves, roots originating in transgenic plants or their progeny previously transformed by means of the method of the invention and therefore consisting at least in part of transgenic cells, are also an object of the present invention.

The following examples are illustrative but not limiting of the present invention.

Deposition of Biological Material

*E. coli* strains carrying the expression cassettes according to the present invention have been deposited under the Budapest Treaty with the Deutsche Sammlung von Mikroorganismen und Zellkulturen (DSMZ) in Braunschweig, Germany, under the following Accession Nos.:

| Strain | Accession No. |
| --- | --- |
| PRiceCYC TOP10 (cassette of plasmid B) | DSM 12714 |
| Pbaa142 TOP10 (cassette of plasmid A) | DSM 12713 |

EXAMPLES

Introduction of Provitamin A (β-Carotene) and Xanthophyll Biosynthesis in Carotenoid-Free Rice (*Oryza saliva*) Endosperm Phytoene Formation Burkhardt et al., 1997

Previous biochemical investigations using radiolabelled isopentenyl diphosphate have shown, that rice endosperm possesses enzymatically active GGPP synthase thus providing an important precursor for carotenoid biosynthesis. Therefore the japonica rice model variety Taipei 309 was transformed by microprojectile bombardment with a cDNA coding for phytoene synthase from daffodil (*Narcissus pseudonarcissus*; (Acc. No. X78814, Schledz and Beyer, 1996, Schledz et al., 1996) under the control of a constitutive and under the control of an endosperm specific promoter. In transgenic rice plants the daffodil enzyme was shown to be active by the in vivo accumulation of the non-coloured carotene phytoene in rice endosperm. Thus ist was demonstrated for the first time that it was possible in principle to engineer the first carotenoid specific enzymatic step in carotenoid biosynthesis in a non-photosynthetic, carotenoid-lacking tissue.

Figure 4:
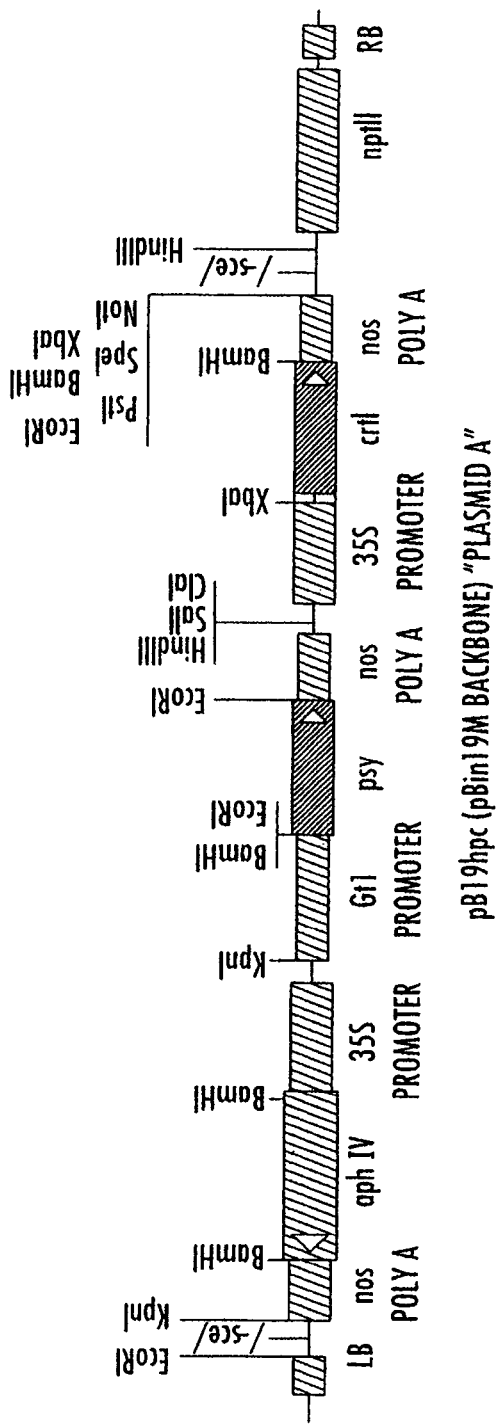
FIG. 4 schematically illustrates the expression cassettes used in "plasmid A" and "plasmid B". LB, left border; RB, right border; psy, phytoene synthase, cDNA from *Narcissus pseudonaicissus*; crtI, carotene desaturase gene from *Erwinia uredovora*; cyc, lycopene cyclase, cDNA from *Narcissus pseudonarcissus*; aphIV, hygromycin phosphotransferase; Gt1, rice glutelin1 promoter; 35S, CaMV 35S promoter; nos, nopaline synthase terminator; NptII, kanamycin-resistance gene.
Figure 4:
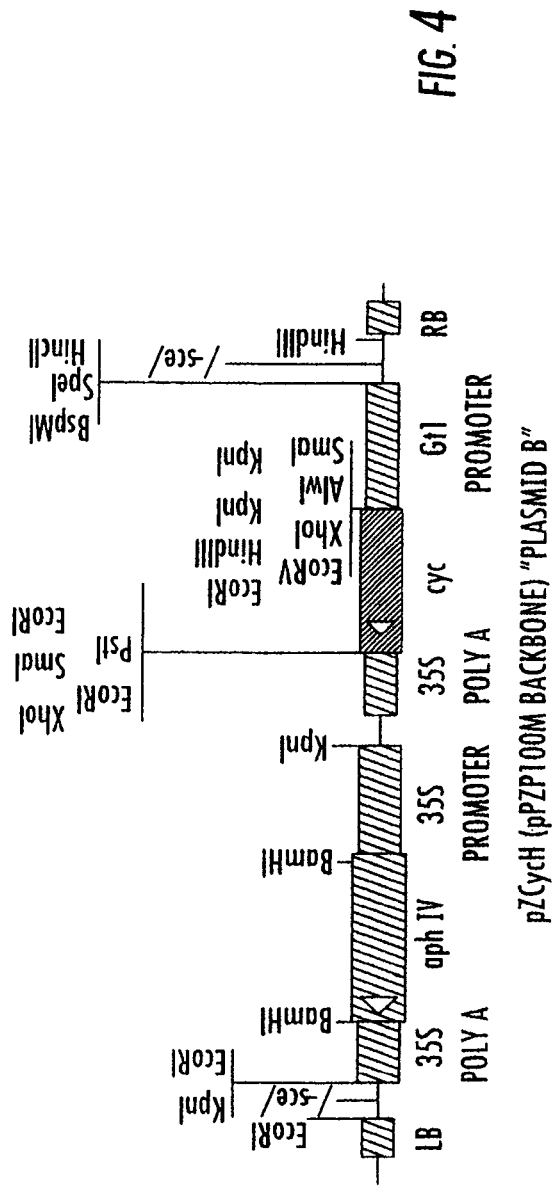

Introduction of the Carotenoid Biosynthetic Pathway Towards Lycopene, β-Carotene (Provitamin A) and Xaxthophylls into Rice Endosperm Plasmid Construction (For standard molecular biological techniques see Sambrook et al., 1989. For a schematic representation of the constructs, see FIG. 4). The structural genes coding for carotenoid biosynthetic enzymes were:

Psy: phytoene synthase from *Narcissus pseudonarcissus* (Acc. No. X78814).

crtI: carotene desaturase from the bacterium *Erwinia uredovoral* fused to the transit sequence of the pea Rubisco (Misawa et al., 1993).

cyc: lycopene cyclase from *Narcissus pseudonarcissus* (Acc. No. X 98796).

Construction of pB19hpc (Termed "Plasmid A" in the Text):

A DNA-fragment carrying the intact phytoene desaturase gene (crtI) from *Erwinia uredovora* with the transit peptide sequence of the pea Rubisco small subunit (tp) downstream of the CaMV 35S-promotor and upstream of the nos 3' polyadenylation signal has been constructed by Misawa et al. (1993) and ligated into HindIII/EcoRI digested pUC19 to obtain the plasmid pUCET4. The crtI expression cassette was excised from pUCET4 as a HindIII/EcoRI-fragment and ligated into HindIII/EcoRI digested pBluescriptKS, yielding the plasmid pBaaI1. The plasmid pGt1PsyH (Burckhardt et al., 1997) carrying a psy expression cassette consisting of phytoene synthase cDNA from *Narcissus pseudonarcissus* (Acc. No. X78814) under the control of the rice glutelin 1 promoter (Gt1; Kim et al., 1993; Okita et al., 1989; Zheng et al., 1993) and the nos 3' polyadenylation signal was digested with SacII and blunt ended by using T4-DNA polymerase. To obtain the psy expression cassette, a second digest with KpnI was carried out. The SacII(blunted)/KpnI fragment was then ligated into XhoI(blunted)/KpnI digested pBaaII to obtain the plasmid pBaaI2 carrying a critI and psy expression cassettes.

The polylinker sites of pUC18 were replaced to contain the following restriction sites in the following order: Hind III, I-SceI, KpnI, NotI, SmaI, IsceI, EcoRI. The resulting plasmid pUC18M was digested with KpnI and NotI. A DNA fragment carrying the crtI and psy expression cassettes was excised from pBaaI2 using KpnI and NotI and ligated in the digested pUC18M mentioned above. The plasmid obtained pBaaI3, contains the double expression cassettes flanked by two meganuclease restriction sites (I-SceI).

The hygromycin phosphotransferase gene aph IV expression cassette containing of aph IV under the control of CaMV35S promoter and CaMV 35S polyadenylation signal was excised from pRice (see construction of plasmid B) as a KpnI fragment and ligated into with KpnI digested pBaaI3. The obtained plasmids pBaaI42 and pBaaI41 contain the hygromycin resistance cassette in the same orientation like the psy expression cassette (pBaaI42) or in the opposite orientation (pBaaI41).

The vector pBin19 (Bevan, 1984) was digested with EcoRI and HindIII and a synthetic oligonucleotide sequence containing the following restriction sites in the following order: Hind III, I-Scel, KpnI, NotI, SmaI, IsceI, EcoRI was introduced using standard protocol, which made up pBin19M.

The expression cassettes of crtI, psy and aph IV were excised from pBaaI42 using the meganuclease sites I-sceI and ligated into pBin19M after digestion with I-sceI. The resulting plasmid pB19hpc was then used for transformation.

Construction of pZCycH (Termed "Plasmid B" in the Text):

The glutelin 1 promoter Gt1 was excised from pKS1(Okita et al., 1989) using EcoRI/BglII and ligated into BamHI/MunI digested pV34 (Füttere and Potrykus, unpublished) between two I-Scel meganuclease sites to obtain the plasmid pV34Gt1. The hygromycin phosphotransferase gene aph IV expression cassette containing of CaMV 35S polyadenylation signal followed by aph IV under the control of CaMV35S promoter and a second CaMV 35S polyadenylation signal after was excised from pCIB900 (Wünn et al., 1996) using SalI and SacI. After ligation of an XhoI adapter to the SalI site to the obtained fragment the cassette was ligated into pV34Gt1 to obtain the Plasmid (pRice). The *lycopene cyclase cyc* from *Narcissus pseudonarcissus* (Acc. No. X 98796) was excised from the plasmid pGEM4CYC (Bonk et al., 1997) using Ecl136II and BamHI. After treatment with Klenow fragment the cyc was ligated into Ecl136II digested pRice to obtain pRiceCYC.

The vector pPZP100 (Hajdukiewicz et al., 1994) was digested with EcoRI and HindIII and a synthetic oligonucleotide sequence containing the following restriction sites in the following order: Hind III, I-SceI, KpnI, NotI, SmaI, IsceI, EcoRI was introduced using standard protocol, which made up pPZP100M.

The cyc aphIV double cassette was excised from pRiceCYC using the IsceI meganuclease and ligated into IsceI digested pPZP100M to obtain the transformation plasmid pZCycH.

Callus Induction and Transformation

Callus induction: Immature seeds of japonica rice cultivar TP 309 at milk stage were collected from greenhouse-grown plants, surface-sterilized in 70% ethanol (v/v) for 1 min, incubated in 6% calcium hypochloride for one hour on a shaker and rinsed 3-5 times with sterile distilled water. Immature embryos were then isolated from the sterilized seeds under binocular microscope in air-flow clean bench and cultured onto NB medium (N6 salts and B5 vitamins, supplemented with 30 g/l maltose, 500 mg/l proline, 300 mg/l casein hydrolate, 500 mg/l glutamine, and 2 mg/l 2,4-D, pH5.8). After 4-5 days the coleoptiles were removed, and the swelled scutella were subcultured onto fresh NB medium for 3-5 days until inoculation of *Agrobacterium*.

*Agrobacterium*-mediated transformation: One week old precultured immature embryos were immersed in *Agrobacterium tumefaciens* LBA 4404 cell suspension as described (Uze et al. 1997). For co-transformation of the two separate vectors, pZPsC and pZCycH, LBA4404/pZPsC ($OD_{600}$=2.0) mixed with equal volume of LBA4404/pZCycH ($OD_{600}$=1.0) after acetonsyrigone induction was used for inoculation. The inoculated precultured embryos were co-cultivated onto NB medium supplemented with 200 mM acetosyringone for 3 days, subcultured on recovery medium (NB with 250 mg/l cefotaxime) for one week and then transferred onto NB selection medium in presence of 30 mg/l hygromycin and 250 mg/l cefotaxime for 4-6 weeks. Plants were regenerated from recovered resistant calli on NB medium supplemented with 0.5 mg/l NAA and 3 mg/l BAP in 4 weeks, rooted and transferred into greenhouse.

Southern Blotting

To prove for the presence of the transgenes Southern blots were carried out according to standard methods (Sambrook et al. (1989) using the homologous labelled probes derived from phytoene synthase, CrtI and cyclase.

Carotenoid Pigment Analyses

Seeds (1 g) from R0-plants were dehusked and treated for 8 h with emery-paper on a shaker, to remove the seed coat. By visual inspection transformed lines showed a clearly detectable yellowish colour due to the presence of carotenoids. Moreover, a segregation pattern was detectable being in some cases very close to the expected 3(yellow) to 1 (white) ratio.

Figure 3A:
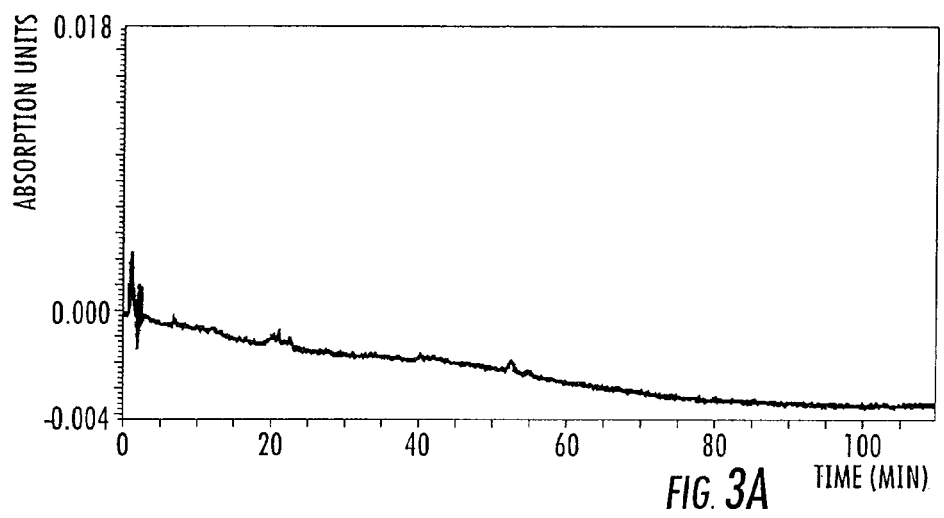
FIG. 3 gives HPLC analyses of polished rice seeds (the endosperm) from untransformed (FIG. 3A) and transformed (with plasmid A, FIG. 3B; with plasmid A plus B, FIG. 3C) rice plants. The appearance of carotenoids, cyclic carotenes and xanthophylls, is evident in the traces representing transformed seeds.
Figure 3B:
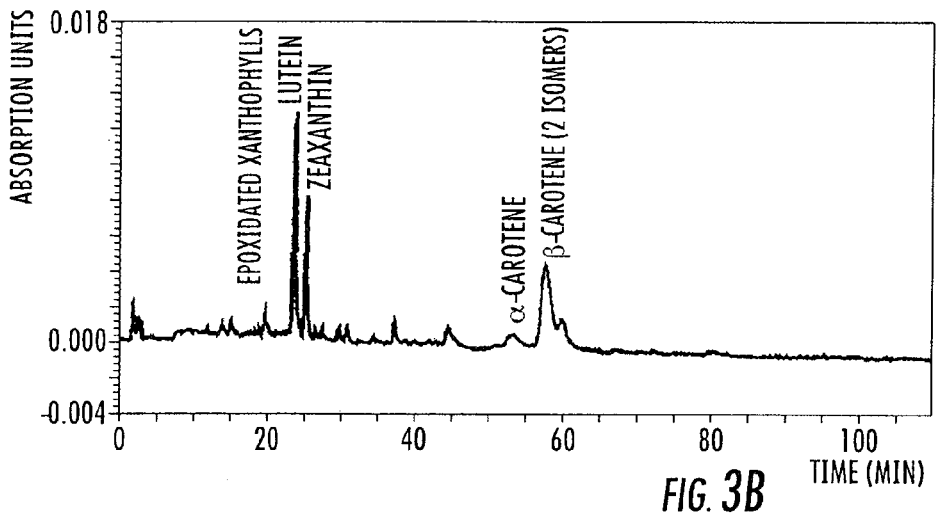
Figure 3C:
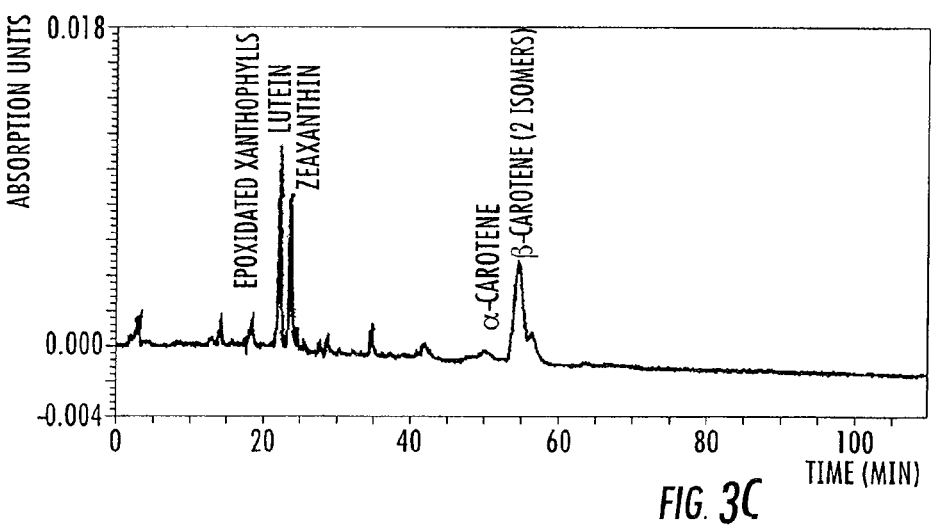

The sum of seeds from individual lines (50, each) were ground to a fine powder using a micro dismembrator (Braun, Melsungen). This was extracted repeatedly with acetone to complete decolorization. The combined extracts were dried under a stream of nitrogen. The residue was dissolved in chloroform and applied quantitatively to HPLC analysis using a Waters HPLC system equipped with a photodiode array detector and a $C_{30}$ reversed phase column (YMC Europe GmbH). Separation was carried out using the solvent system A: MeOH:tert Butylmethyl ether (1:1, v/v) B: MeOH: tert Butylmethyl ether:$H_2O$ (6:1.2:1.2, v/v/v) using a gradient 100% B to 43% B within 25 min then to 0% B within further 75 min. These final conditions were maintained for additional 10 min prior to re-equilibration. Examples for the results obtained is given in FIG. 3A for an untransformed control, in FIG. 3B for a line carrying only plasmid A and in FIG. 3C for a line carrying plasmid A and. Evidently, carotenoids are accumulated in the transformants. The controls sometimes exhibited some trace amounts of carotenoids which can to their largest part be attributed to the seed coat which is difficult to remove completely. Among the carotenoids detected in the transformed seeds, β-carotene (provitamin A) represents the main product (up to 60%). In addition, the xanthophyll-forming pathway was active leading to the formation of lutein and zeaxanthin, as well as of some amounts of epoxidated carotenoids. It is concluded that this later part of the pathway is either induced by the transformation or by products derived from the transformation. Alternatively the xanthophyll-forming pathway is constitutively expressed in rice endosperm, resulting in the formation of the xanthophylls zeaxanthin and lutein plus some additional minor components representing epoxidated xanthophylls.

Lines transformed with plasmid A alone, showed in principle the same carotenoid pattern, however the carotenoid content was generally lower so that the above conclusions are extended to lycopene cyclase in rice endosperm.

Especially the presence of lutein and zeaxanthin are regarded as an unexpected added value due to their positive effects e.g. in vision (see e.g. Brown et al., 1998; Schalch, 1992).

Obviously, many modifications and variations of the present invention are possible in the light of the above teachings. It is, therefore, to be understood that within the scope of the appended claims, the invention may be practised otherwise than as specifically described.

The Precursor Geranylgeranyl Diphosphate Occurs Ubiquitously in Plant Material

To test for the presence of GGPP in other tissues than rice, incubation experiments were carried out analogously as described for rice endosperm with endosperm isolated from two laboratory varieties of wheat, two varieties of barley and Cavendish banana fruit. Immature wheat and barley grains were dehusked, the endosperm was squeezed-off and the embryo removed. Incubation experiments were carried out in 100 mM Tris/HCl buffer pH 7.4, 10 mM $MgCl_2$, 1 mM $MnCl_2$, 3 mM ATP in the presence of 0.5 µCi [1-$^{14}$C]isopentenyl diphosphate for 6 h at 25° C. The individual assays were supplemented with alkaline phosphatase to allow dephosphorylation of the prenyl-diphosphates formed. After 3-6 h, lipid-soluble material including the corresponding prenyl-alcohols were isolated by chloroform/methanol (2/1, v/v) extraction. This was followed by HPLC analysis, as given above In endosperm from the wheat varieties examined (both being essentially carotenoid-free), a very pronounced signal was observed which, by using authentic dephosphorylated GGPP (produced with the aid of recombinant GGPP synthase from *Sinapis alba*) proved to represent geranylgereaniol. Thus, the installation by transformation of provitamin A biosynthesis into wheat appears as feasible as in rice. Smaller but detectable amounts of GGPP in the form of the corresponding alcohol were observed in barley as an expression of the fact that barley endosperm exhibits some small background of carotenoid formation. Similarly, Cavendish banana produce carotenoids and therefore the presence of GGPP-forming activities that were especially observed in a ripe state were not surprising.

CPTA Inducing Carotenoid Biosynthesis Genes

The long known lycopene cyclase inhibitor CPTA (2-(4-chlorphenylthio)triethylamine hydrochloride) and related compounds (see e.g. El-Sayed Osman et al., 1984; Fosket and Radin, 1982) mimicks, with respect to lycopene accumulation the transformation with plasmid A. Seeking to demonstrate an up-regulation of carotenoid biosynthetic genes, we synthesized CPTA according to the method given by Scheutz and Baldwin (1957) applied this compound in an 1 mM aqueous solution to daffodil flowers. This photosynthetically inactive tissue responded by accumulating lycopene, as expected. However, inexplicable by the primary action of CPTA (an inhibitor!) the carotenoid content was almost doubled. Therefore, Northern and Western Blot analyses were carried out to demonstrate a possible induction of the abundance in transcripts coding for carotenoid biosynthetic enzymes or in abundance of enzymes.

Figure 5A:
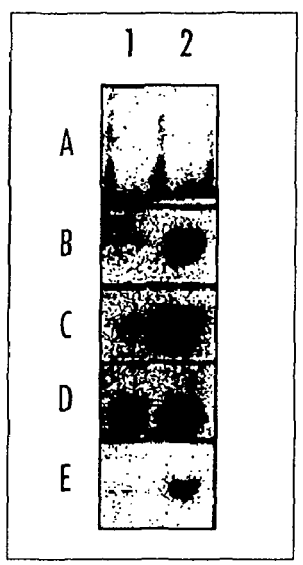
FIG. 5: A, Northern blot using RNA from untreated (lane 1) and CPTA-treated (lane 2) daffodil flowers. The immobilized RNA was stripped repeatedly to allow hybridization using labelled probes for B, phytoene synthase; B, phytoene desaturase; C, ζ-carotene desaturase; E, lycopene cyclase. B, Western blot using protein extracts from untreated (lane 1) and treated (lane 2) daffodil flowers. The blots were probed with antibodies directed against A, phytoene synthase; B, phytoene desaturase; C, ζ-carotene desaturase; D, lycopene cyclase.

FIG. 5A gives the results of the Northern blots. Total RNA was isolated from untreated (lane 1) and CPTA-treated flowers. The immobilized RNA was repeatedly stripped to allow subsequent hybridization with probes for phytoene synthase (B), phytoene desaturase (C), ζ-carotene desaturase and lycopene cyclase. It is evident that, with the exemption of ζ-carotene desaturase, all specific carotenogenic RNAs, including lycopene cyclase are increased in abundance.

Figure 5B:
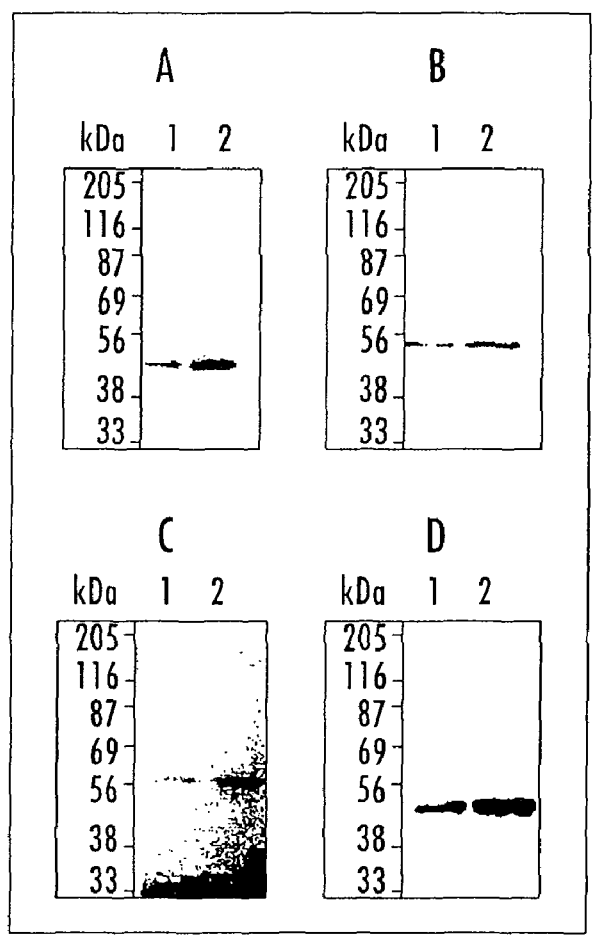

For Western blot analysis (see FIG. 5B), total protein was isolated from untreated and CPTA-treated flowers and, following SDS polyacrylamide gel electrophoresis (30 µg protein per lane), transferred to nitrocellulose membranes. The blots were the developed with antibodies directed against phytoene synthase (A), phytoene desaturase (B), ζ-carotene desaturase (C) and lycopene cyclase. It is evident that at the protein level an increase in enzyme abundance takes place upon CPTA-treatment.

With the rice date given above we conclude that carotenoids (or products derived thereof) can genetically induce the formation of carotenoids in a sort of feedback-mechanism.

The present invention thus provides means by genetic engineering to introduce the carotenoid biosynthetic pathway into carotenoid-free tissues or to enhance the productivity of pre-existing carotenoid biosynthetic pathways. The method can be used to improve the nutritional value, pharmacology of visual appearance of seeds, fruit, tubers, flowers or leaves.

The invention is primarily useful in improving nutritional demands, where it is not particularly relevant to produce large amounts of carotenoids. Rice, for example, in its milled form consists of the endosperm, which does not contain detectable coloured carotenoids. These are present in the seed coat that is removed during processing. This processing is required to enable long-term storage of rice grains.

This invention represents the first example of a de-novo engineering of a carotenoid biosynthetic pathway, and is applicable to other tissues of agronomically important carotenoid-free crops, for example other cereal seeds, or to root tissues that are free of coloured or uncoloured carotenoids. This does not exclude the potential of the method to increase or modify pre-existing carotenoids.

REFERENCES CITED

Albrecht et al. (1996) *Eur. J. Biochem.* 236, 115-120
Allison et al. (1986) *Virology* 154, 9-20
Armstrong et al. (1989) *Mol. Gen. Genet.* 216, 254-268
Armstrong et al. (1990), *Proc. Natl. Acad. Sci. USA* 87, 9975-9979
Bartley et al. (1999) *Eur. J. Biochem.* 259, 396-403
Ballas et al. (1989), *Nucl. Acids Res.* 17, 7891-7903
Bevan et al., (1983) *Nature* 304, 184-187
Bevan (1984) *Nucl. Acid Res.* 3, 138-140
Bevan et al. (1986) *Nucl. Acid Res.* 14, 4625-4638

Beyer et al. (1989) *Eur. J Biochem.* 184, 141-150
Bird et al. (1991) *Biotechnology* 9, 635-639
Bonk et al. (1997) *Eur. J Biochem.* 247, 942-950
Bouvier et al. (1989) *Biochem. Biophys. Acta* 1391:320-328
Bouvier et al. (1996) *J. Biol. Chem.* 271, 28861-28867
Bramley et al. (1992) *Plant J.* 2, 343-349
Bray (1987) *Planta* 172, 364-370
Britton, G. (1988) Biosynthesis of carotenoids p. 133-182, In T. W. Goodwin (ed.). Plant Pigments, 1988. Academic Press, Inc. (London)
Brown et al. (1998) *Eye* 12, 127-33
Bugos and Yamamoto (1996) *Proc. Natl. Acad. Sci. USA* 93, 6320-6325
Burkhardt et al. (1997) *Plant J.* 11, 1071-1078
Chamovitz et al. (1991) *Plant Mol. Biol.* 16, 967-974
Christou et al (1988) *Plant Physiol* 87, 671-674
Clark et al (1989) *J. Biol. Chem.* 264, 17544-17550
Cornejo et al (1993) *Plant Mol. Biol.* 23, 567-581
Crossway et al. (1986) *Bio Techniques* 4, 320-334
Cunningham et al. (1996) *Plant Cell* 8, 1613-26
Cunningham et al. *FEBS Lett.* 238, 130-138
Datta et al. (1990) *Biotechnology* 8, 736-740
Della-Cioppa et al. (1987) *Plant Physiol.* 84, 965-968
Dogbo et al. (1988) *Proc. Natl. Acad. Sci. USA,* 85:7054-7058
Elroy-Stein et al. (1989) *Proc. Natl. Acad. Sci. USA* 86, 6126-6130
El-Sayed et al. (1984) *Ann. Bot.* 53, 21-27
Firek et al. (1993) *Plant Molec. Biol.* 22, 192-142
Fosket and Radin, (1983) *Plant Sci. Lett.* 30, 165-175
Fray and Grierson (1993) *Plant Mol. Biol* 22, 589-602
Fray et al. (1995) *Plant J* 8, 693-701
Fromm et al. (1990) *Biotechnology* 8, 833-839
Gallie et al. (1989) *Molecular Biology of RNA,* 237-256
Gordon-Kamm et al. (1990) *Plant Cell* 2, 603-618
Grant (1991) *The Sate of the World's Children.* Oxford University Press, Oxford
Gruber et al. (1993) in: *Methods in Plant Molecular Biology and Biotechnology* 89-119 (CRC Press).
Guerineau et al. (1991) *Mol. Gen. Genet.* 262, 141-144
Hajdukiewicz et al. (1994) *Plant Mol Biol.* 25, 989-994
Hinchee et al. (1988) *Biotechnology* 6, 915-921
Hoekemenn et al. (1983) *Nature* 303, 179-180
Hoever et al. (1994) *Transgenic Res.* 3, 159-166
Hoshino et al. (1993) *Appl. Environ. Microbiol* 59, 3150-3153
Hugueney et al. *Eur. J Biochem.* 209, 39-407.
Humphrey et al. (1992). *WHO Bulletin* 70:225-232
Hundle et al. (1994) *Mol. Gen. Genet* 214, 374-385.
Jobling and Gehrke (1987) *Nature* 325, 622-625
Joshi et al. (1987) *Nucl. Acids Res.* 15, 9627-9639
Kay et al. (1987) *Science* 236, 1299
Kim et al. (1993) *Plant Cell Physiol.* 34, 595-603
Klein et al. (1988a) *Proc. Natl. Acad. Sci. USA* 85, 4305-4309
Klein et al. (1988b) *Plant Physiol.* 91, 440-444
Linden et al. (1991) *Z. Natwiforsch.* 46c, 1045-1051
Logemann et al. (1989) *Plant Cell* 1, 151-158
Lommel et al. (1991) *Virology* 81, 382-385
Luehrsen and Walbot (1991) *Mol. Gen. Genet.* 225, 81-93
Macejak and Sarnow (1991) *Nature* 353, 90-94
Marin et al. (1996) *EMBO J.* 15, 2331-2342
Masamoto et al. (1998) *Plant Cell Physiol* 39, 560-4
Mayer et al. (1990) *Eur. J Biochem.* 191, 359-363
McBride et al. (1994) *Proc. Natl. Acad. Sci. USA* 97, 7301-7305
McCabe et al. (1988) *Biotechnology* 6, 923-926
McCormick et al. (1986) *Plant Cell Reports* 5, 81-84
Misawa et al. 1990, *J Bacteriol.* 172, 6704-6712
Misawa et al. (1993) *Plant J* 4, 833-840
Mogen et al. (1990) *Plant Cell* 2, 1261-1272
Muller et al. (1990) *Mol. Gen. Genet* 224, 136-146
Munroe et al. (1990) *Gene* 91, 151-158
Marray et al. (1989) *Nucl. Acids. Res.* 17, 477-498
Neuhaus et al. (1987) *Theor. Appl. Genet.* 75, 30-36
Nievelstein et al. (1995) *Eur. J Biochem* 233, 864-872
Norris et al. (1995) *Plant Cell* 7, 2139-2149
Okita et al. (1989) *J Biol. Chem* 264, 12573-12581
Pasamontes et al. (1997) *Gene* 185, 35-41
Pecker et al. (1992) *Proc. Nail Acad. Sci. USA* 89, 4966-4966
Pedersen et al. (1982) *Cell* 29, 1015-1026
Perlak et al. (1991) *Proc. Natl. Acad. Sci* 88, 3324-3328
Proudfoot (1991) *Cell* 64, 671-674
Riggs et al. (1986) *Proc. Natl. Acad. Sci* 83, 5602-5606
Rohrmeier and Lehle (1993) *Plant Mol. Biol.* 22, 783-792
Romer et al. (1993) *Biochem Biophys. Res. Comintin.* 196, 1414-1421
Sambrook et al. (1989) Molecular Cloning: A Lab. Manual, 2nd, Cold Spring Lab. Press, Cold Spring Harbor.
Sanford et al. (1987) *Particulate Science and Technology* 5, 27-37
Sanford et al. U.S. Pat. No. 4,945,050
Sanfacon et al. (1991) *Gened Dev.* 5, 141-149
Schalch (1992) EXS62, 280-298
Scheutz and Baldwin (1957) *Proc. Acad. Chem. USA* 80, 162-164
Schledz M. and Beyer P. (1996) *Plant Physiol.* 110, 336
Schledz et al. (1996) *Plant J* 10, 781-792
Schulz, et al. (1993) *FEBS Lett.* 318, 162-166
Scolnik and Bartley (1995) *Plant Physiol.* 108, 1342
Shah et al. (1986) *Science* 233, 478-481
Stanford et al. (1989)*Mol. Gen. Genet.* 215, 200-208
Staub and Maliga (1993) *EMBO J.* 12, 601-606
Sommer (1988) *J Nutr.* 119, 96-100
Sun et al. (1996) *J Biol. Chem,* 271, 24349-52
Svab et al. (1990) *Proc. Natl. Acad. Sci. USA* 87, 8526-8530
Svab and Maliga (1993) *Proc. Natl. Acad. Sci. USA* 90, 913-917
Thompson et al. (1987) *EMBO J.* 6, 2519-2523
Uze et al. (1997) *Plant Sci.* 130, 87-95
Van den Elzen et al. (1985) *Plant Mol. Biol.* 5, 299-392
Velten et al. (1984) *EMBO J* 3, 2723-2730
Von Heijne et al. (1991) *Plant Mol. Biol. Rep.* 9, 104-126
Wang et al. (1988) *Plant Mol. Biol.* 11, 433-439
Warner et al. (1993) *Plant J.* 3, 191-201
Weissinger et al. (1988) *Annual. Rev. Genet.* 22, 421-477
Wuenn et al. (1996) *Bio Technol.* 14, 171-176
Yanish-Perron et al. (1985) *Gene* 33, 103-109
Xu et al. (1993) *Plant Mol. Biol.* 22, 573-588
Zheng et al. (1993) *Plant J.* 4, 357-366

The invention claimed is:

1. A method of producing price cells, selected from the group consisting of rice endosperm cells, rice embryo cells and rice plant cells, that accumulate β-carotene which cells are normally carotenoid-free said method comprising transforming plant material with an isolated DNA molecule comprising a nucleotide sequence which comprises:
    (a) an expression cassette capable of directing production in said cells of a phytoene synthase derived from a plant; and
    (b) an expression cassette capable of directing production in said cells of a phytoene desaturase derived from a bacteria; and
    selecting transformed plant material that comprises the cells that accumulate β-carotene.

2. A method according to claim 1 wherein said phytoene desaturase is from the CrtI gene of *Erwinia uredovora*.

3. A method according to claim 1 wherein said phytoene desaturase is fused with a suitable plastid transit peptide.

4. A method according to claim 1 wherein said phytoene desaturase is expressed under the control of a tissue specific or constitutive promoter.

5. A method according to claim 4 wherein said phytoene desaturase is expressed under the control of a constitutive promoter.

6. A method according to claim 1 wherein said phytoene synthase is expressed under the control of a tissue specific promoter.

7. A method according to claim 6 wherein said phytoene synthase is derived from *Narcissus pseudonarcissus*.

8. A method according to claim 1 wherein said DNA further comprises a polynucleotide which provides for a selectable marker.

9. A method according to claim 1 wherein said plant material is transformed via an *Agrobacterium* which comprises said DNA.

10. A transformed rice plant cell obtainable by a method of claim 1.

11. A method of producing rice plants that accumulate β-carotene in endosperm cells, said method comprising transforming plant material with an isolated DNA molecule comprising a nucleotide sequence which comprises:
   (a) an expression cassette capable of directing production in said cells of a phytoene synthase derived from a plant; and
   (b) an expression cassette capable of directing production in said cells of a phytoene desaturase derived from a bacteria;
   and selecting transformed plant material that comprises the cells that accumulate β-carotene.

* * * * *

UNITED STATES PATENT AND TRADEMARK OFFICE
CERTIFICATE OF CORRECTION

| | | |
|---|---|---|
| PATENT NO. | : 7,838,749 B2 | Page 1 of 1 |
| APPLICATION NO. | : 12/144224 | |
| DATED | : November 23, 2010 | |
| INVENTOR(S) | : Beyer | |

It is certified that error appears in the above-identified patent and that said Letters Patent is hereby corrected as shown below:

At column 20, in claim 1, at line 54, delete "price" and insert therefor --rice--

Signed and Sealed this
Twenty-second Day of March, 2011

David J. Kappos
*Director of the United States Patent and Trademark Office*